United States Patent [19]

Bilofsky et al.

[11] 4,279,983
[45] Jul. 21, 1981

[54] SILVER IMAGE STABILIZATION

[75] Inventors: Ruth C. Bilofsky, Lexington; Mara O. Nestle, Natick, both of Mass.

[73] Assignee: Polaroid Corporation, Cambridge, Mass.

[21] Appl. No.: 143,439

[22] Filed: Apr. 24, 1980

Related U.S. Application Data

[63] Continuation-in-part of Ser. No. 33,003, Apr. 24, 1979, abandoned.

[51] Int. Cl.³ .......................... G03C 5/54; G03C 5/38; G03C 1/48; G03C 7/00
[52] U.S. Cl. ................................. 430/228; 430/233; 430/245; 430/248; 430/428; 430/463; 430/612
[58] Field of Search ............... 430/228, 233, 245, 248, 430/428, 447, 463, 612

[56] References Cited

U.S. PATENT DOCUMENTS

| | | | |
|---|---|---|---|
| 3,326,684 | 6/1967 | Nishio et al. | 430/428 |
| 3,704,126 | 11/1972 | Land et al. | 430/233 |
| 3,730,716 | 5/1973 | Land et al. | 430/233 |
| 3,821,000 | 6/1974 | Land et al. | 430/233 |

*Primary Examiner*—Richard L. Schilling
*Attorney, Agent, or Firm*—Philip G. Kiely

[57] ABSTRACT

A novel photographic film unit, preferably a diffusion transfer film unit adapted to provide silver images of enhanced image stability which comprises photosensitive silver halide, silver precipitating nuclei and a stabilizing compound consisting of a noble metal complexed with a ligand, said ligand being adapted to hydrolyze in aqueous alkali to provide a diffusible complex of said noble metal.

26 Claims, No Drawings

SILVER IMAGE STABILIZATION

CROSS-REFERENCE TO OTHER APPLICATIONS

This application is a continuation-in-part of application Ser. No. 33,003, filed Apr. 24, 1979, now abandoned.

BACKGROUND OF THE INVENTION

Procedures for preparing photographic images in silver by diffusion transfer principles are well known in the art. For the formation of the positive silver images, a latent image contained in an exposed photosensitive silver halide emulsion is developed and almost concurrently therewith, a soluble silver complex is obtained by reaction of a silver halide solvent with the unexposed and undeveloped silver halide of said emulsion. Preferably, the photosensitive silver halide emulsion is developed with a processing composition in a viscous condition which is spread between the photosensitive element comprising the silver halide emulsion and a print-receiving element comprising, preferably, a suitable silver-precipitating layer. The processing composition effects development of the latent image in the emulsion and, substantially contemporaneously therewith, forms a soluble silver complex, for example, a thiosulfate or thiocyanate, with undeveloped silver halide. This soluble silver complex is, at least in part, transported in the direction of the print-receiving element and the silver thereof is largely precipitated in the silver-precipitating element to form a positive image thereon. Procedures of this description are disclosed, for example, in U.S. Pat. No. 2,543,181 issued to Edwin H. Land. See, also, Edwin H. Land, *One Step Photography*, Photographic Journal, Section A, pp. 7–15, January 1950.

Additive color reproduction may be produced by exposing a photosensitive silver halide emulsion through an additive color screen having filter media or screen elements each of an individual additive color, such as red or green or blue, and by viewing the reversed or positive silver image formed by transfer to a transparent print-receiving element through the same or a similar screen which is suitably registered with the reversed or positive image carried by the print-receiving layer.

As examples of suitable film structures for employment in additive color photography, mention may be made of U.S. Pat. Nos. 2,861,885; 2,726,154; 2,944,894; 3,536,488; 3,615,427; 3,615,428; 3,615,429; 3,615,426; and 3,894,871. Diffusion transfer film units are known wherein there is contained a positive transfer image and a negative silver image, the two images being in the same or separate layers on a common, transparent support and viewed as a single, positive image. Such positive images may be referred to for convenience as "integral positive-negative images", and more particularly as "integral positive-negative transparencies". Examples of film units which provide such integral positive-negative transparencies are set forth, for example, in the above-indicated U.S. Pat. Nos. 3,536,488; 3,894,871; 3,615,426; 3,615,427; 3,615,428; and 3,615,429.

In general, silver-precipitating nuclei comprise a specific class of adjuncts well known in the art as adapted to effect catalytic reduction of solubilized silver halide specifically including heavy metals and heavy metal compounds such as the metals of Groups IB, IIB, IVA, VIA and VIII and the reaction products of Groups IB, IIB, IVA and VIII metals with elements of Group VIA. Particularly preferred precipitating agents are noble metals such as silver, gold, platinum, palladium, etc., and are generally provided in a matrix as colloidal particles.

U.S. Pat. No. 3,647,440, issued Mar. 7, 1972 discloses receiving layers comprising finely divided non-silver noble metal nuclei obtained by reducing a noble metal salt in the presence of a colloid or binder material with a reducing agent having a standard potential more negative than $-0.30$.

Copending application Ser. No. 649,201, filed Jan. 14, 1976 (commonly assigned), now abandoned and replaced by continuation application Ser. No. 69,282, filed Aug. 24, 1979 discloses and claims a receiving element for use in an additive color photographic diffusion transfer film unit which comprises a transparent support carrying an additive color screen and a layer comprising noble metal silver-precipitating nuclei and a polymer; wherein the nuclei are present at a level of about $0.1$–$0.3$ mgs/ft$^2$, and said polymer is present at a level of from about 0.5 to 5 times the coverage of said nuclei. Preferably, the noble metal is obtained by reduction of a noble metal salt or complex, and more preferably, the noble metal is palladium.

Copending application Ser. No. 897,942, filed Apr. 4, 1978 (commonly assigned), now U.S. Pat. No. 4,186,013, issued Jan. 29, 1980, discloses and claims a receiving element for use in a silver diffusion transfer film unit which comprises a support carrying a layer of noble metal silver-precipitating nuclei in a polymeric binder composition of polyvinyl alcohol and gelatin.

Copending application Ser. No. 897,943, filed Apr. 4, 1978 (commonly assigned), now U.S. Pat. No. 4,186,015, issued Jan. 29, 1980, discloses and claims a receiving element for use in a silver diffusion transfer film unit which comprises a support carrying a layer of noble metal silver-precipitating nuclei in a binder composition of hydroxyethyl cellulose and gelatin.

Enhanced image stability can be provided to silver images by the employment of noble metal compounds containing a noble metal below silver in the Electromotive Force Series of Elements. A preferred system also includes the employment of an $\alpha,\beta$-enediol silver halide developing agent. Film units and processes disclosing and claiming such stabilization systems are set forth in U.S. Pat. Nos. 3,704,126; 3,730,716 and 3,821,000.

In selecting the specific noble metal compound, consideration must be given to the ligand. For example, one must be selected that will not deleteriously affect the sensitometry of the film unit and one which will control the migration of the noble metal compound from its initial location in the film unit to the developed silver image at the appropriate rate and time. Thus, a noble metal compound migrating too slowly may result in poor silver image stability in that the delay would permit drying or separation of the silver image from the remainder of the film unit before sufficient transfer of noble metal compound to adequately stabilize the silver image. On the other hand, a compound moving too rapidly, i.e., before silver image formation is essentially complete, could interfere with the development of either or both of the positive and negative silver images thereby adversely affecting sensitometry.

This invention also provides novel noble metal compounds adapted to provide such enhanced stability to silver images which compounds are not taught or suggested by the prior art.

SUMMARY OF THE INVENTION

The present invention is directed to photographic film units and processes employing a noble metal compound adapted to provide enhanced stability to a silver image, said noble metal compound or complex being substantially non-diffusible until the ligand is hydrolyzed, said compound consisting of a noble metal complexed with a ligand adapted to hydrolyze in aqueous alkali to provide a diffusible complex of said noble metal. Such compounds are particularly suitable for use in silver diffusion transfer film units, and have been found to provide more efficient use of the noble metal than prior art compounds.

DETAILED DESCRIPTION OF THE INVENTION

The stabilizing compounds employed in the present invention are substantially insoluble and non-diffusible in the film unit in which they are disposed prior to being hydrolyzed by the alkaline processing composition during processing. The hydrolysis produces a diffusible complex of the noble metal which is then able to migrate to the silver image. This delayed availability of the noble metal complex thus provides a diffusible noble metal complex formed at a rate adpated to avoid deleterious interaction with other components of the film unit and which then diffuses to provide enhanced stability to the reduced silver image without adversely affecting the sensitometry.

The stabilizing compounds of the present invention may be disposed in various locations in the film unit, such as, for example, the photosensitive layer, the image-receiving layer or a separate layer.

As stated above, the stabilizing compounds employed in the present invention consist of a noble metal complexed with a ligand. The ligand is further defined as one which, upon contact with aqueous alkali, undergoes a hydrolysis to provide a diffusible complex of the noble metal which then migrates to the silver metal image to provide the desired stabilization.

The specific noble metal complex selected for any given film is determined by several factors which are ascertained empirically within the scope of this invention. Thus, the selection of the particular ligand is determined by the rate of hydrolysis of the noble metal complex in the particular aqueous alkaline processing composition. The rate of hydrolysis which provides the diffusible noble metal complex in turn, is determined by the desired amount of time for the noble metal complex to reach the silver image. The diffusion or migration of the noble metal complex must not be so rapid that it interferes with the development of the silver image.

A particularly preferred class of compounds adapted for use in this invention, which compounds are novel per se, are represented by the formula

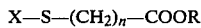

X—S—(CH$_2$)$_n$—COOR wherein X is a noble metal more noble than silver, i.e., below silver in the Electromotive Force Series of Elements, n is 1, 2 or 3 and R is an alkyl group which may be removed by alkaline hydrolysis. The length of the alkyl group, and the nature of substituents thereon, (e.g., solubilizing groups such as hydroxyl or carboxyl), may be selected to provide the rate of hydrolysis desired for any particular film system. In the preferred embodiments of this invention R is a 1 to 4 carbon alkyl group. Suitable noble metals include gold, palladium and platinum. A particularly preferred compound is the gold (I) complex of methylthioglycolate, AuSCH$_2$COOCH$_3$.

For simplicity, the preferred stabilizing compound of the present invention is represented as complexed with a monovalent noble metal, e.g., Au$^{+1}$. It will be understood that, depending upon the noble metal employed, the number of —S—(CH$_2$)$_n$—COOR ligands associated therewith will be determined by the valency or coordination number of the noble metal.

Specific compounds within the scope of the present invention are set forth below.
1. AuSCH$_2$COOCH$_3$
2. AuSCH$_2$CH$_2$COOCH$_3$
3. AuSCH$_2$CH$_2$COOC$_4$H$_9$
4. AuSCH$_2$COOC$_4$H$_9$ The preferred compounds of the present invention are prepared by reacting an alkyl mercaptoalkylate with a noble metal compound in a suitable solvent.

"Suitable solvents" refers to solvents for both the alkyl mercaptoalkylate and the noble metal compound starting material. Such solvents include ethanol, methanol, isopropanol and ethyl ether. The products need not be dried after synthesis but can be used as a dispersion.

The following non-limiting example illustrates the preparation of the preferred compound within the scope of the present invention.

EXAMPLE 1

3.50 g of methyl thioglycolate were dissolved in 100 cc of methanol and added to a blender. 3.94 g of tetrachloroauric acid were dissolved in 50 cc of methanol and added to the methyl thioglycolate solution with rapid stirring. The mixture immediately turned dark orange, and a precipitate formed. Stirring was continued until the orange color had disappeared leaving a white precipitate in a pale yellow solution. The mixture was filtered and the resulting white paste was returned to the blender with approximately 100 cc of methanol. This mixture was stirred vigorously for approximately ten minutes and then filtered. This washing and filtration procedure was repeated three more times, once with methanol and then twice with water. The white paste obtained (6.3) was added to 20 g of distilled water and was stirred for approximately five minutes. 0.95 g of a 10% aqueous solution of Daxad 11 were added and the mixture was stirred to effect mixing. The mixture was sonicated maintaining a temperature of 40° C. or less for 20 minutes. 4.7 g of 10% gelatin solution were added and the mixture was sonicated at 40° C. or less for an additional 10 minutes. The resulting dispersion was employed for disposing the stabilizing compound in the film unit described below.

In general, the optimum concentration of the noble metal stabilizing compound will be determined empirically for each specific film unit system. Since the novel compound of the present invention utilizes the noble metal more efficiently than prior art compounds, relatively small concentrations need be employed in the film unit. In general, the preferred range of compound utilized is about 5 to 100 mgs of noble metal per g of silver present in the photosensitive silver halide layer which generally falls in the range of about 0.5–10 mgs/ft² of the gold complex of alkylthioalkylate compound.

As stated above, the noble metal stabilizing compound may be disposed in various locations in the film unit. Suitable film units include, but are not limited to, those described in the patents and applications set forth above. Thus, the present invention includes film units comprising a photosensitive silver halide layer and a silver precipitating nuclei-containing image-receiving layer adapted to provide positive silver image formation by diffusion transfer processing, wherein the image-receiving layer may be maintained in superposed relationship with the negative image or separated therefrom, and film units wherein the silver precipitating nuclei are in the photosensitive silver halide layer. The noble metal compound may be located in whole or in part in a separate layer adjacent to the layer in which the image silver is to be located or directly in the image-receiving layer.

As will readily be recognized, additional layers or functions may optionally be included in the film unit such as, for example, a separate layer retaining the noble metal compound of the present invention as well as spacer layers, barrier layers, timing layers, protective layers, neutralizing layers, stripping layers, antihalation layers and support layers.

In the preferred embodiment of the present invention, the film unit comprises a support preferably transparent to actinic radiation and carrying on a first surface a photosensitive silver halide layer, a layer containing silver precipitating nuclei dispersed therein and, for color image reproduction, an additive color screen interposed between the transparent support and the photosensitive silver halide layer.

EXAMPLE A

A film unit was prepared comprising a transparent polyester film base carrying on one surface, an additive color screen of approximately 1500 triplets per inch of red, blue and green filter screen elements in repetitive side-by-side relationship; 328 mgs/ft² polyvinylidine chloride/polyvinyl formal protective overcoat layer; a nucleating layer comprising palladium nuclei at a coverage of 0.15 mgs/ft² gelatin and 1.0 mgs/ft² hydroxyethyl cellulose; an interlayer formed by coating 1.9 mgs/ft² gelatin, 2.3 mgs/ft² acetic acid and 0.19 mgs/ft² octylphenoxy polyethoxy ethanol surfactant; a hardened gelatino silver iodobromo emulsion (a 50–50 blend of 0.59µ and 0.72µ mean diameter grains) coated at a coverage of about 69.4 mgs/ft² of gelatin and about 84 mgs/ft² of silver with about 3.25 mgs/ft² propylene glycol alginate and about 0.55 mgs/ft² of nonyl phenol polyglycol ether (containing 9.5 moles of ethylene oxide) and 18.9 mgs/ft² of a carboxylated styrene/butadiene copolymer latex (Dow 620, Dow Chemical Company, Midland, Michigan); panchromatically sensitized with 5,5'-dimethyl-9-ethyl-03,3'-bis-(3-sulfopropyl)thiacarbocyaninetriethyl-ammonium salt(0.53 mg/gAg);
5,5'-diphenyl-9-ethyl-3,3'-bis-(4-sulfobutyl)oxacarbocyanine (0.75 mg/gAg);
anhydro-5,6-dichloro-1,3-diethyl-3'-(4"-sulfobutyl)benzimidazolothiacarbocyanine hydroxide (0.7 mg/gAg); and
3-(3-sulfopropyl)-3'-ethyl-4,6-benzo-thia-thiacyanine betaine (1.0 mg/gAg); red, green, green and blue sensitizers respectively; and the following antihalo top coat.

| Top Coat | mgs/ft² |
|---|---|
| Gelatin | 400 |
| Dow 620 (carboxylated styrene/butadiene copolymer latex Dow Chemical Co., Midland, Michigan) | 204 |
| Propylene glycol alginate | 25.7 |
| Dioctyl ester of sodium sulfosuccinate | 1.2 |
| Daxad-11 (polymerized sodium salts of alkyl naphthalene sulfonic acid) Manufactured by W. R. Grace & Co. Cambridge, MA | 0.38 |
| Pyridinium bis-1,5 (1,3-diethyl-2-thiol-5-barbituric acid) pentamethine oxanol (Ag salt) | 5.6 |
| 4-(2-chloro-4-dimethylamino benzaldehyde)-1-(p-phenyl carboxylic acid)-3-methyl pyrazolone-5 | 7 |

| PROCESSING COMPOSITION | Weight % |
|---|---|
| Sodium hydroxide | 8.43 |
| Hydroxyethyl cellulose (Sold by Hercules, Inc., Wilmington, Delaware under the tradename Natrasol 250 H H) | |
| Tetramethyl reductic acid | 0.64 |
| Potassium bromide | 0.62 |
| 2-methylthiomethyl-4,6-dihydroxypyrimidine | 7.04 |
| 4-aminopyrazolo-[3,4d]-pyrimidine | 0.02 |
| N-benzyl-α-picolinium bromide (50% solution) | 3.52 |
| Sodium tetraborate . 10H₂O | 3.31 |
| Glycerin | 1.63 |
| p-isononylphenoxypolyglycidol (containing about 10 glycidol units) | 0.50 |
| Sodium sulfite | 0.82 |
| Water | 66.4 |

Film units were prepared by the above procedure except that the top coat contained, as designated below, (a) no noble metal stabilizing compound; (b) a prior art stabilizing compound; or (c) stabilizing compound within the scope of the present invention.

The film units were given a 16 mcs exposure with a Xenon sensitometer and processed with mechanical rollers with an 0.8 mil gap disposing the above-described processing composition between the top coat and a polyethylene terephthalate cover sheet. The film unit was held in the dark for one minute and then the cover sheet was removed, retaining the rest of the film unit together and then drying.

The spectral data were obtained by reading the neutral column to red, green and blue light in an automatically recording densitometer on film units immediately after processing, and after subjection to two different accelerated aging tests.

The following tables summarize the data:

TABLE 1

| EXAMPLE NO. | STABILIZER | GOLD COVERAGE | INITIAL R | $D_{Max}/D_{Min}$ G | B |
|---|---|---|---|---|---|
| 2(Control) | None | 0 | 3.06/0.52 | 3.47/0.57 | 3.60/0.66 |
| 3(Control) | None | 0 | 2.86/0.37 | 3.10/0.42 | 3.13/0.45 |
| 4(Control) | Benzimidazole 2-thiol gold complex | 5 mg/ft$^2$ | 2.77/0.32 | 3.06/0.35 | 3.02/0.36 |
| 5(Control) | Benzimidazole 2-thiol gold complex | 5.6 mg/ft$^2$ | 3.18/0.45 | 3.38/0.49 | 3.38/0.49 |
| 6 | AuSCH$_2$CO- | 0.63 mg/ft$^2$ | 3.03/0.35 | 3/06/0.35 | 3.08/0.36 |
| 7 | AuSCH$_2$COOCH$_3$ | 1.5 mg/ft$^2$ | 3.46/0.51 | 3.35/0.46 | 3.26/0.46 |
| 8 | AuSCH$_2$COOCH$_3$ | 2.1 mg/ft$^2$ | 2.90/0.38 | 2.95/0.43 | 2.95/0.37 |
| 9 | AuSCH$_2$CH$_2$CH$_3$ | 5 mg/ft$^2$ | 3.49/0.54 | 3.39/0.50 | 3.13/0.50 |
| 10 | AuSCH$_2$CH$_2$COOCH$_3$ | 1.77 mg/ft$^2$ | 3.25/0.48 | 3.35/0.54 | 3.34/0.51 |
| 11 | AuSCH$_2$CH$_2$COOCH$_3$ | 5.44 mg/ft$^2$ | 3.12/0.52 | 3.25/0.53 | 3.24/0.51 |
| 12 | AuSCH$_2$CH$_2$COOC$_4$H$_9$ | 0.95 mg/ft$^2$ | 2.62/0.42 | 2.80/0.45 | 2.89/0.47 |
| 13 | AuSCH$_2$CH$_2$COOC$_4$H$_9$ | 2.98 mg/ft$^2$ | 2.67/0.42 | 2.76/0.43 | 2.81/0.44 |
| 14 | AuSCH$_2$CH$_2$COOH | 0.4 mg/ft$^2$ | 3.24/0.46 | 3.38/0.50 | 3.11/0.50 |
| 15 | AuSCH$_2$CH$_2$COOH | 1.3 mg/ft$^2$ | 3.0/0.046 | 2.77/0.49 | 2.74/0.44 |
| 16 | AuSCH$_2$COOC$_4$H$_9$ | 1.7 mg/ft$^2$ | 3.02/0.46 | 3.11/0.52 | 3.00/0.50 |
| 17 | AuSCH$_2$COOC$_4$H$_9$ | 5.3 mg/ft$^2$ | 3.06/0.46 | 3.10/0.49 | 2.96/0.46 |
| 18 | AuSCH$_2$COOH | 0.9 mg/ft$^2$ | 2.26/0.42 | 2.32/0.56 | 2.37/0.58 |

TABLE 2

| EXAMPLE NO. | STABILIZER | GOLD COVERAGE | 120° F. OVEN $\Delta D_{Max}/\Delta D_{Min}$ | | | | 100° F., 80% RELATIVE HUMIDITY $\Delta D_{Max}/\Delta D_{Min}$ | | | |
|---|---|---|---|---|---|---|---|---|---|---|
| | | | DAYS | R | G | B | DAYS | R | G | B |
| 2(Control) | None | 0 | 1 | +0.05/+0.01 | +0.02/+0.01 | +0.01/0.0 | 1 | −.57/−.01 | −0.36/−0.03 | −0.22/+0.03 |
| | | | 5 | +0.04/+0.03 | +0.04/+0.03 | 0.0/−0.01 | 5 | −0.65/−0.03 | −0.40/+0.04 | −0.27/−0.01 |
| | | | 10 | +0.03/0.02 | +0.01/0.03 | −0.05/−0.01 | 10 | −0.65/−0.03 | −0.44/0.0 | −0.34/−0.05 |
| | | | 20 | +0.03/+0.02 | +0.01/+0.01 | −0.05/−0.04 | | | | |
| 3(Control) | None | 0 | 1 | +0.02/+0.02 | +0.01/+0.10 | +0.02/+0.05 | 5 | −0.52/−0.04 | −0.21/0.0 | −0.03/−0.05 |
| | | | 5 | −0.03/+0.01 | 0.0/+0.01 | −0.01/0.0 | 10 | −0.58/−0.04 | −0.30/0.0 | −0.10/0.05 |
| | | | 10 | −0.05/0.0 | −0.02/+0.01 | −0.03/0.0 | 15 | −0.28/+0.01 | | −0.12/−0.05 |
| | | | 18 | −0.10/0.0 | −0.05/0.0 | −0.05/−0.01 | 20 | −0.58/−0.03 | −0.33/−0.03 | −0.22/−0.10 |
| | | | | | | | 10 | −0.60/−0.03 | | |
| 4(Control) | Benzimidazole 2-thiol gold complex | 5 mg/ft² | 1 | −0.02/0.0 | −0.02/0.0 | −0.02/0.0 | 1 | +0.20/+0.01 | +0.10/+0.07 | 0.0/+0.04 |
| | | | 5 | −0.06/0.0 | −0.07/0.0 | −0.08/0.0 | 5 | +0.19/+0.01 | +0.10/+0.10 | −0.02/+0.08 |
| | | | 10 | −0.05/0.0 | −0.05/0.0 | −0.17/−0.01 | 10 | +0.22/+0.02 | +0.14/+0.12 | +0.08/+0.08 |
| | | | 15 | −0.05/+0.03 | −0.07/0.0 | −0.14/−0.03 | 20 | +0.22/0.02 | +0.11/+0.09 | −0.09/+0.04 |
| 5(Control) | Benzimidazole 2-thiol gold | 5.6 mg/ft² | 5 | +0.02/+0.03 | +0.03/+0.03 | −0.03/+0.01 | 1 | −0.01/+0.01 | +0.03/+0.06 | +0.02/+0.04 |
| | | | 10 | +0.03/+0.03 | +0.04/+0.03 | +0.02/+0.01 | 5 | +0.02/+0.02 | +0.06/+0.08 | −0.01/+0.04 |
| | | | 15 | +0.03/+0.03 | +0.04/+0.03 | −0.04/0.0 | 10 | +0.03/+0.03 | +0.05/+0.07 | −0.04/+0.02 |
| | | | 20 | +0.03/+0.02 | +0.03/+0.02 | +0.01/0.0 | 13 | +0.03/+0.03 | +0.05/+0.07 | −0.06/+0.02 |
| | | | 25 | +0.01/+0.03 | +0.03/+0.01 | +0.02/−0.01 | | | | |
| 6 | AuSCH₂COOCH₃ | 0.63 mg/ft² | | | | | 1 | −0.03/0.0 | +0.06/0.07 | +0.05/+0.03 |
| | | | | | | | 5 | −0.13/0.0 | +0.02/+0.07 | 0.0/0.04 |
| | | | | | | | 10 | −0.13/0.0 | +0.05/+0.08 | −0.01/+0.04 |
| | | | | | | | 20 | −0.14/+0.01 | 0.0/+0.06 | −0.08/+0.01 |
| 7 | AuSCH₃OOCH₃ | 1.5 mg/ft² | 5 | −0.07/+0.02 | −0.08/+0.01 | −0.03/+0.02 | 5 | 0.0/+0.03 | +0.09/+0.11 | −0.05/+0.07 |
| | | | 30 | −0.10/+0.04 | −0.04/+0.03 | −0.01/+0.04 | 30 | +0.05/+0.04 | +0.05/+0.12 | −0.04/+0.10 |
| 8 | AuSCH₃COOCH₃ | 2.1 mg/ft² | 1 | −0.01/0.0 | −0.01/0.0 | −0.02/0.0 | 1 | +0.10/−0.02 | +0.19/+0.09 | +0.05/+0.05 |
| | | | 5 | −0.02/0.0 | −0.03/0.0 | −0.04/0.0 | 5 | +0.04/+0.01 | +0.13/+0.09 | +0.02/+0.09 |
| | | | 10 | −0.02/+0.02 | −0.03/+0.01 | −0.09/−0.02 | 10 | +0.05/+0.01 | +0.05/+0.09 | +0.01/+0.08 |
| | | | 15 | −0.03/+0.02 | −0.06/−0.01 | −0.12/−0.05 | 15 | +0.04/+0.03 | +0.13/+0.09 | −0.06/+0.05 |
| 9 | AuSCH₂COOCH₃ | 5 mg/ft² | 1 | +0.02/0.0 | −0.02/0.0 | 0.0/0.0 | 5 | −0.03/0.05 | 0.06/+0.10 | −0.01/+0.08 |
| | | | 5 | +0.01/+0.02 | +0.03/+0.02 | 0.0/0.0 | | | | |
| | | | 10 | +0.01/+0.01 | +0.01/+0.01 | −0.08/−0.01 | | | | |
| | | | 20 | −0.02/+0.01 | −0.03/0.0 | −0.08/−0.03 | | | | |
| | | | 28 | 0.0/ | 0.0/−0.03 | 0.0/−0.03 | | | | |
| 10 | AuSCH₂CH₂COOCH₃ | 1.77 mg/ft² | 1 | +0.04/+0.01 | +0.03/+0.01 | +0.06/+0.01 | 1 | −0.03/0.0 | −0.01/+0.01 | −0.01/+0.01 |
| | | | 5 | +0.05/+0.02 | +0.04/+0.04 | +0.06/+0.02 | 5 | −0.15/0.0 | −0.04/+0.05 | −0.05/+0.02 |
| | | | 10 | +0.06/+0.02 | +0.06/0.0 | +0.02/+0.01 | 10 | −0.18/+0.01 | −0.07/+0.08 | −0.07/+0.04 |
| | | | 20 | +0.06/+0.03 | +0.08/0.0 | +0.04/+0.01 | | | | |
| | | | 28 | +0.02/0.0 | +0.04/0.0 | +0.04/+0.01 | | | | |
| 11 | AuSCH₂CH₂COOCH₃ | 5.44 mg/ft² | 1 | −0.05/−0.02 | −0.05/−0.02 | −0.04/−0.01 | 1 | −0.01/+0.01 | +0.02/+0.03 | 0.0/+0.02 |
| | | | 5 | −0.03/−0.01 | −0.04/−0.03 | −0.02/−0.02 | 5 | −0.07/+0.04 | +0.12/+0.13 | 0.0/+0.09 |
| | | | 10 | −0.03/−0.01 | −0.02/−0.02 | −0.02/−0.02 | 10 | −0.08/+0.06 | +0.12/+0.16 | 0.0/+0.10 |
| | | | 24 | −0.03/−0.01 | 0.0/−0.02 | −0.02/−0.02 | | | | |
| 12 | AuSCH₂CH₂COOC₄H₉ | 0.95 mg/ft² | 1 | −0.05/−0.01 | −0.07/−0.01 | −0.04/−0.01 | 1 | −0.05/0.0 | −0.04/+0.01 | −0.01/0.00 |
| | | | 5 | −0.03/0.0 | −0.06/0.0 | −0.04/−0.01 | 5 | −0.05/0.0 | −0.04/+0.01 | −0.01/0.00 |
| | | | 10 | −0.02/0.0 | −0.03/+0.01 | −0.03/−0.01 | 10 | −0.30/−0.01 | −0.26/+0.05 | −0.20/+0.02 |
| 13 | AuSCH₂CH₂COOC₄H₉ | 2.98 mg/ft² | 1 | −0.05/0.0 | −0.07/−0.01 | −0.04/−0.01 | 1 | −0.04/0.0 | −0.02/+0.01 | −0.02/0/0 |
| | | | 5 | −0.03/0.0 | −0.06/0.0 | −0.03/−0.01 | 5 | −0.17/−0.01 | −0.08/+0.04 | −0.07/0.0 |
| | | | 10 | −0.02/0.0 | −0.03/+0.01 | −0.02/0.0 | 10 | −0.21/−0.01 | −0.12/+0.05 | −0.10/+0.02 |
| | | | 24 | −0.03/0.0 | −0.02/0.0 | −0.02/−0.02 | | | | |

TABLE 2-continued

| EXAMPLE NO. | STABILIZER | GOLD COVERAGE | DAYS | 120° F. OVEN $\Delta D_{Max}/\Delta D_{Min}$ | | | DAYS | 100° F., 80% RELATIVE HUMIDITY $\Delta D_{Max}/\Delta D_{Min}$ | | |
|---|---|---|---|---|---|---|---|---|---|---|
| | | | | R | G | B | | R | G | B |
| 14 | AuSCH$_2$CH$_2$-COOCH | 0.4 mg/ft$^2$ | 1 | 0.0/0.0 | −0.05/0.0 | −0.04/0.0 | 1 | −0.13/0.0 | −0.09/+0.01 | −0.02/−0.02 |
| | | | 10 | −0.01/0.00 | −0.05/+0.02 | −0.05/+0.01 | 7 | −0.48/0.0 | −0.14/+0.07 | 0.00/+0.05 |
| | | | 20 | −0.01/0.0 | −0.02,+0.04 | −0.06/+0.03 | 13 | −0.49/−.03 | −0.17/+0.04 | −0.03/+0.02 |
| 15 | AuSCH$_2$CH$_2$-COOCH | 1.3 mg/ft$^2$ | 1 | −0.01/−0.01 | −0.02/0.0 | −0.02/−0.01 | 1 | −0.13/+0.01 | 0.0/+0.02 | −0.02/+0.0 |
| | | | 10 | −0.03/−0.02 | −0.01/+0.02 | −0.02/+0.02 | 10 | −0.37/0.0 | −0.01/+0.07 | +0.05/+0.01 |
| | | | 20 | −0.06/+0.03 | −0.06/+0.04 | −0.06/+0.03 | 13 | −0.37/+0.01 | −0.05/+0.06 | +0.02/+0.02 |
| 16 | AuSCH$_2$-COOC$_4$H$_9$ | 1.7 mg·ft$^2$ | 1 | +0.01/0.0 | +0.1/−0.01 | 0.0/0.0 | 1 | −0.13/+0.01 | 0.0/+0.02 | −0.02/+0.01 |
| | | | 5 | +0.05/−0.02 | +0.03/−0.02 | +0.1/0.0 | 5 | −0.36/0.0 | +0.01/+0.05 | +0.05/+0.01 |
| | | | 12 | +0.07/−0.01 | +0.11/−0.01 | +0.08/+0.01 | 12 | −0.52/0.0 | −0.03/+0.07 | +0.08/+0.01 |
| 17 | AuSCH$_2$-COOC$_4$H$_9$ | 5.3 mg/ft$^2$ | 1 | +0.01/0.0 | 0.0/0.0 | 0.0/0.0 | 1 | −0.03/0.0 | +0.02/+0.01 | +0.01/0.0 |
| | | | 5 | +0.02/−0.02 | 0.0/−0.01 | 0.0/0.0 | 5 | −0.16/+0.01 | +0.13/+0.05 | +0.04/+0.02 |
| | | | 12 | −0.01/−0.01 | +0.05/0.0 | +0.05/+0.02 | 12 | −0.21/+0.01 | +0.12/+0.07 | +0.06/+0.03 |
| 18 | AuSCH$_2$-COOH | 0.9 mg/ft$^2$ | | | | | 1 | −0.01/0.0 | −0.02/0.0 | −0.01/0.0 |
| | | | | | | | 5 | −0.04/0.0 | −0.06/−0.02 | −0.04/−0.01 |

In considering the above tables, it will be seen that the most severe test is the 100° F., 80% R.H. It will be seen that the prior art gold compound, benzimidazole-2-thiol gold complex, provides significantly enhanced stability to the silver image compared to the control as indicated by the small $\Delta D_{max}/D_{min}$ values. In fact, it will be noted that in many instances a slight increase in density is noted. However, even an increase in density can be undesirable if the change is not consistant, i.e., if all the densities do not increase accordingly. The most effective level of the benzimidazole-2-thiol gold complex was 5.61 mg/ft$^2$ (as gold).

The gold salt of methyl thioglycolate at very low levels, i.e., 0.63 mg/ft$^2$ and 1.5 mg/ft$^2$ (as gold) (Examples 6 and 7) are found to be as effective as the higher benzimidazole-2-thiol gold complex levels. At 5 mg/ft$^2$ as gold the gold salt of methyl thioglycolate produces superior stability to the above stated prior art compound. It should also be noted that employing the compounds of the present invention eliminates the presence of any uncomplexed ligand or compound preparation by-products which might be injurious to the photosensitive system since the uncomplexed ligand is readily removed and the by-products are photographically harmless.

It should also be noted that the advantages of the present invention are not achieved by use of the free acid form of ligand, e.g., Examples 14, 15 and 18 which shows significant loss of density under conditions of high heat and humidity.

U.S. Pat. No. 3,730,716 discloses and claims the employment of a noble metal stabilizing compound with a silver halide developing agent whose oxidation product is substantially non-oxidative to the silver image for a time sufficient to enable the noble metal ion to contact the silver image to provide sustained and long lasting stabilization effects. The novel stabilizers of the present invention are particularly suitable for use in such a system.

While the present invention has been described primarily in terms of additive color systems, it should be understood that the present invention is also suitable for use in black and white silver diffusion transfer systems.

The support or film base employed may comprise any of the various types of transparent rigid or flexible supports, for example, glass, polymeric films of both the synthetic type and those derived from naturally occurring products, etc. Especially suitable materials, however, comprise flexible transparent synthetic polymers such as polymethacrylic acid, methyl and ethyl esters; vinyl chloride polymers; polyvinyl acetals; polyamides; polyesters such as the polymeric films derived from ethylene glycol and terephthalic acid; cellulose derivatives such as cellulose, acetate; polycarbonates; polystyrenes; and the like.

The additive color screen employed in the present invention may be formed by techniques well known in the art, e.g., by sequentially printing the requisite filter patterns by photomechanical methods. An additive color screen comprises an array of sets of colored areas or filter elements, usually from two to four different colors, each of said sets of colored areas being capable of transmitting visible light within a color filter element that transmits light within one of the so-called primary wavelength ranges, i.e., red, green and blue. A regular mosaic of this type may be made by the alternating embossing and doctoring technique described in U.S. Pat. No. 3,019,124. The additive color screen also may be composed of minute dyed particles, such as starch grains or hardened gelatin particles, intermixed and interspersed in a regular or random arrangement to provide a mosaic. Another method of forming a suitable color screen comprises multi-line extrusion of the type disclosed in U.S. Pat. No. 3,032,008, the colored lines being deposited side-by-side in a single coating operation. Still another method is set forth in U.S. Pat. No. 3,284,208.

Silver halide solvents useful in forming the desired soluble complex with unexposed silver are well known and, for example, may be selected from the alkali metal thiosulfates, particularly sodium or potassium thiosulfates, or the silver halide solvent may be a cyclic imide, such as uracil, in combination with a nitrogenous base as taught in U.S. Pat. No. 2,857,274 issued Oct. 21, 1958, to Edwin H. Land; or pseudo-uracils, such as the 4,6-dihydroxypyrimidines as taught in U.S. Pat. No. 4,126,459, issued Nov. 21, 1978. While the silver halide solvent is preferably initially present in the processing composition, it is within this invention to initially position the silver halide solvent in a layer of the film unit, preferably in the form of a precursor which releases or generates the silver halide solvent upon contact with an alkaline processing fluid.

The processing composition may contain a thickening agent, such as an alkali metal carboxymethyl cellulose or hydroxyethyl cellulose, in a quantity and viscosity grade adapted to facilitate application of the processing composition. The processing composition may be left on the processed film or removed, in accordance with known techniques, as is most appropriate for the particular film use. The requisite alkalinity, e.g., a pH of 12-14, is preferably imparted to the processing composition by an alkaline material such as sodium, potassium and/or lithium hydroxide. A wetting agent may be advantageously included in the processing composition to facilitate application thereof, particularly where the processing composition is applied in a very thin layer of low viscosity fluid.

Suitable silver halide developing agents may be selected from amongst those known in the art, and may be initially positioned in a layer of the photosensitive element and/or in the processing composition. Organic silver halide developing agents are generally used, e.g., organic compounds of the benzene or naphthalene series containing hydroxyl and/or amino groups in the para- or ortho-positions with respect to each other, such as hydroquinone, tert-butyl hydroquinone, toluhydroquinone, p-aminophenol, 2,6-dimethyl-4-aminophenol,2,4,6-triaminophenol, etc. If the silver image, e.g., additive color transparency is not washed after processing to remove unused silver halide developing agent, development reaction products, etc., the silver halide developing agent(s) should not give rise to colored reaction products which might stain the image or which, either unreacted or reacted, might adversely affect the stability and sensitometric properties of the final image. Particularly useful silver halide developing agents having good stability in alkaline solution are substituted reductic acids, particularly tetramethyl reductic acid, as disclosed in U.S. Pat. No. 3,615,440 issued Oct. 26, 1971 to Stanley M. Bloom and Richard D. Cramer, and $\alpha, \beta$-enediols as disclosed in U.S. Pat. No. 3,730,716 issued to Edwin H. Land, Stanley M. Bloom and Leonard C. Farney on May 1, 1973.

Having thus described the invention, what is claimed is:

1. A photographic silver diffusion transfer film unit which comprises photosensitive silver halide, silver precipitating nuclei and a stabilizing compound consisting of a noble metal complexed with a ligand, said ligand being adapted to hydrolyze in aqueous alkali to provide a diffusible complex of said noble metal.

2. The film unit of claim 1 wherein said stabilizing compound is $$XS(CH_2)_nCOOR$$

wherein X is a noble metal below silver in the Electromotive Force Series of Elements n is 1, 2 or 3 and R is an alkyl or substituted alkyl group removable by alkaline hydrolysis.

3. The film unit of claim 2 wherein R is a 1 to 4 carbon alkyl group.

4. The film unit of claim 2 wherein X is gold, palladium or platinum.

5. The film unit of claim 4 wherein said support is transparent.

6. The film unit of claim 5 which includes an additive color screen intermediate said transparent support and said other layers.

7. The film unit of claim 2 wherein said compound is $AuSCH_2COOCH_3$.

8. The film unit of claim 2 wherein said compound is $AuSCH_2CH_2COOCH_3$.

9. The film unit of claim 1 wherein said film unit comprises a support carrying on one surface a layer comprising silver precipitating nuclei and a layer comprising photosensitive silver halide crystals.

10. The film unit of claim 9 wherein said stabilizing compound is disposed in said layer containing said photosensitive silver halide crystals.

11. The film unit of claim 9 wherein said stabilizing compound is disposed in a layer adjacent said layer containing said photosensitive silver halide crystals.

12. The film unit of claim 9 which includes a common support and wherein said layer containing silver precipitating nuclei is positioned intermediate said support and said photosensitive silver halide layer.

13. The film unit of claim 9 wherein said photosensitive silver halide layer and said layer containing said silver precipitating nuclei are carried on separate supports.

14. The film unit of claim 13 wherein said film unit additionally includes a stripping layer intermediate said layer containing said silver precipitating nuclei and said photosensitive silver halide layer containing said silver halide.

15. The film unit as defined in claim 9 which includes a processing composition permeable layer substantially devoid of silver halide and silver precipitating agents disposed on the surface of the film unit most distant from said support, said permeable layer having said stabilizing compound disposed therein.

16. The film unit as defined in claim 9 which includes an additive color screen.

17. The film unit of claim 1 wherein said stabilizing compound is present at a level of about 5 to 100 mgs of noble metal per g of silver.

18. A silver diffusion transfer photographic process which comprises, in combination, the steps of:
  (a) exposing a photographic film unit comprising photosensitive silver halide and silver precipitating nuclei;
  (b) contacting said exposed film unit with an aqueous alkaline processing composition containing a silver halide developing agent an a silver halide solvent, thereby providing a visible diffusion transfer silver image to said unit, as a function of the point-to-point degree of exposure thereof; and
  (c) contacting said silver image with a soluble complex of a noble metal derived from a stabilizing compound consisting of a noble metal complexed with a ligand, said ligand being adapted to hydrolyze in aqueous alkali whereby said ligand is hydrolyzed in said aqueous alkaline processing composition thereby providing said soluble complex of a noble metal.

19. The process of claim 18 wherein said stabilizing compound is a compound of the formula $$XS(CH_2)_nCOOR$$

wherein X is a noble metal below silver in the Electromotive Force Series of Elements, n is 1, 2 or 3 and R is an alkyl or substituted alkyl group adapted to be removable by alkaline hydrolysis.

20. The process of claim 19 wherein R is a 1–4 carbon alkyl group.

21. The process of claim 19 wherein said compound is $AuSCH_2COOCH_3$.

22. The process of claim 19 wherein said compound is $AuSCH_2CH_2COOCH_3$.

23. The process of claim 18 wherein said compound is present at a level of 5 to 100 mgs of noble metal per g of silver.

24. The process of claim 18 wherein said film unit includes an additive color screen.

25. An additive color diffusion transfer film unit which comprises a transparent support carrying, in order, an additive color screen, a layer comprising palladium metal silver-precipitating nuclei, a photosensitive silver halide emulsion layer; and an antihalation layer; wherein said antihalation layer includes a stabilizing compound consisting of a noble metal complexed with a ligand, said ligand being adapted to hydrolyze in aqueous alkali to provide a diffusible complex of said noble metal.

26. The film unit of claim 25 wherein said stabilizing compound is a compound of the formula $$XS(CH_2)_nCOOR$$

wherein X is a noble metal below silver in the Electromotive Force Series of Elements, n is 1, 2 or 3 and R is an alkyl or substituted alkyl group removable by alkaline hydrolysis.

* * * * *